United States Patent [19]

Buus et al.

[11] 4,153,694
[45] May 8, 1979

[54] BEHENIC ACID ESTERS, COMPOSITIONS THEREOF AND A METHOD OF PREPARATION THEREOF

[75] Inventors: Jørn L. M. Buus, Bjaeverskov; Niels Lassen, Gentofte, both of Denmark

[73] Assignee: Kefalas A/S, Denmark

[21] Appl. No.: 826,049

[22] Filed: Aug. 19, 1977

[30] Foreign Application Priority Data

Aug. 25, 1976 [GB] United Kingdom ............... 35411/76

[51] Int. Cl.² ..................... A61K 31/38; C07D 279/28
[52] U.S. Cl. ...................................... 424/247; 544/42; 544/44
[58] Field of Search .................... 544/42, 44; 424/247, 424/267

[56] References Cited

U.S. PATENT DOCUMENTS 3,966,930 6/1976 Buus et al. ............................. 544/44

FOREIGN PATENT DOCUMENTS 2306074 8/1973 Fed. Rep. of Germany.

OTHER PUBLICATIONS

Chemical Abstracts, vol. 79, abst. no. 149323w (1973) (abst. of Gellr et al., Ger. Offen. 2,306,074).

Primary Examiner—John D. Randolph
Attorney, Agent, or Firm—Gordon W. Hueschen

[57] ABSTRACT

The present invention relates to novel behenic acid esters of the following general formula:

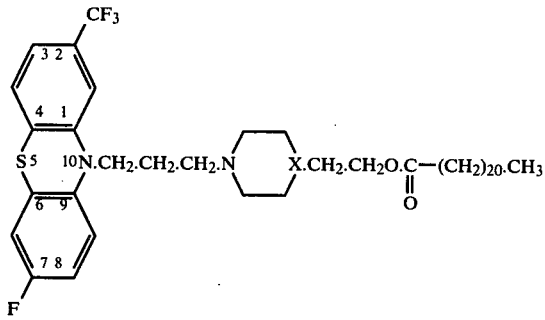

wherein X is "N" or "CH," the non-toxic acid addition salts thereof, a method for the preparation of said esters and therapeutic compositions thereof having prolonged effect.

10 Claims, No Drawings

BEHENIC ACID ESTERS, COMPOSITIONS THEREOF AND A METHOD OF PREPARATION THEREOF

It is an object of the present invention to provide behenic acid esters of Formula I, a method of making the same, a method for the alleviation, palliation, mitigation or inhibition of the manifestations of certain physiological-psychological abnormalities of animals therewith, and pharmaceutical compositions comprising such compounds as active ingredient.

Other objects will be apparent to one skilled in the art and still other objects will become apparent hereinafter.

BACKGROUND OF THE INVENTION

In recent years esters of neuroleptic active phenothiazines have been suggested and found useful in preparations having prolonged effect when administered parenterally, The esters which have been found most useful are enanthic, decanoic and palmitic acid esters of fluphenazine which are mostly administered as sterile solutions in vegetable oils which solutions are injected intramuscularly. The neuroleptic effect of such solutions may last for as long as 15 days.

Also aliphatic carboxylic acid esters of some very strong neuroleptic phenothiazines having a fluorine atom in the 7-position have been suggested and include esters of aliphatic carboxylic acids having up to and including 17 carbon atoms, especially the decanoic and palmitic acid esters.

During continued work with such esters in pharmacological experiments it was found that the decanoic and palmitic acid esters of the very strongly neuroleptic 2-trifluoromethyl-7-fluoro-10-(3'-(4-(2-hydroxyethyl)-1-piperidyl)propyl)phenothiazine and 2-trifluoromethyl-7-fluoro-10-(3'-(4-2-hydroxyethyl)-1-piperazinyl)-propyl)phenothiazine when administered in ordinary doses as oily solutions by injection tended to give too high concentrations at the start causing a pronounced sedation in the first week.

SUMMARY OF THE INVENTION

It has now surprisingly been found that the behenic acid esters of formula I not only have a more prolonged effect but also cause less sedation in the test animals when injected in the form of oily solutions. It also seems that other side effects such as extrapyrimidal symptoms mostly are avoided.

The compounds of formula I may be prepared - according to the method of the invention - by reacting a compound of the following general formula:

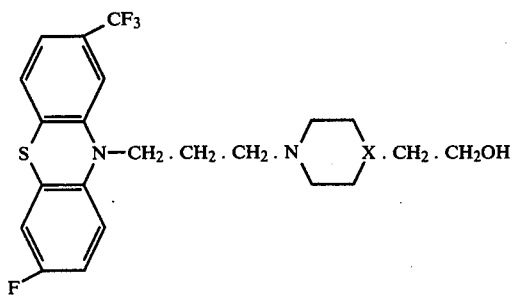

wherein X is as defined before, with a reactive derivative of behenic acid, such as an acid halide or the anhydride, whereupon the compound of formula I formed by the reaction is isolated as the free base or as a non-toxic acid addition salt thereof.

The esterification process according to the invention is preferably carried out in the presence of an inert organic solvent such as a ketone, preferably acetone, or an ether such as diethylether.

The reactive derivative of behenic acid is preferably an acid halide, especially the acid chloride, or the acid anhydride.

The non-toxic acid addition salts of the compounds of formula I are preferably salts of pharmaceutically acceptable acids such as mineral acids, for example hydrochloric acid, hydrobromic acid, phosphoric acid, sulphuric acid, and the like, and organic acids such as acetic acid, tartaric acid, maleic acid, citric acid, methane sulphonic acid, and the like.

The following examples illustrate the method of the invention but may not be construed as limiting:

EXAMPLE 1

The behenic acid ester of 2-trifluoromethyl-7-fluoro-10-(3'-(4-(2-hydroxyethyl)-1-piperidinyl)propyl)phenothiazine 24 grams of 2-trifluoromethyl-7-fluoro-10-(3'-(4-(2-hydroxyethyl)-1-piperidinyl)propyl)phenothiazine, HCl were converted to the corresponding free base in conventional manner. The base was dissolved in 200 milliliters of dry acetone, 40 grams of behenic acid chloride were added and the mixture refluxed on a steam bath for one hour. The reaction mixture was evaporated in vacuum, the residue treated with a mixture of 200 milliliters of water and 200 milliliters of ether, whereupon the ether phase was separated off. The ether phase was then shaken with a cold 10 percent aqueous sodium carbonate solution until alkaline reaction. The ether phase was separated, dried over anhydrous magnesium sulphate and evaporated in vacuum. The residue was crystallized from hexane and consisted of the behenic acid ester of 2-trifluoromethyl-7-fluoro-10-(3'-(4-(2-hydroxyethyl)piperidyl)propyl)phenothiazine, melting at 57–58 degrees Centigrade.

Yield: 22.5 grams.

EXAMPLE 2

The behenic acid ester of 2-trifluoromethyl-7-fluoro-10-(3'-(4-(2-hydroxyethyl)-1-piperazinyl)propyl)phenothiazine.

When example 1 was carried out using 32 grams of 2-trifluoromethyl-7-fluoro-10-(3'-(4'-(2-hydroxyethyl)-1-piperazinyl)-propyl)phenothiazine, 2 HCl instead of 2-trifluoromethyl-7-fluoro-10-(3'-(4-(2-hydroxyethyl)-1-piperidyl)propyl)phenothiazine, HCl the behenic acid ester of 2-trifluoromethyl-7-fluoro-10-(3'-(4-(2-hydroxyethyl)-1-piperazinyl)propyl)-phenothiazine was obtained as a white crystalline substance melting at 62–64 degrees Centigrade.

Yield: 25 grams.

The invention further provides pharmaceutical compositions with prolonged action comprising, as active ingredient, a compound of Formula I or one of its non-toxic acid addition salts together with a pharmaceutical carrier or excipient.

They may be administered to animals, including human beings, both orally, parenterally and rectally, and may take the form of e.g. sterile solutions or suspensions for injection, tablets, suppositories, capsules, and syrups.

Results upon administration to animals, including human beings, of the compositions of the invention have been very gratifying.

Preferably, however, the compositions are in the form of sterile solutions or suspensions for injection, and in a preferred embodiment of the invention injectable solutions may be prepared from a non-toxic injectable fat or oil, e.g. light vegetable oil, sesame oil, olive oil, arachis oil or ethyl oleate, and they may additionally contain gelling agents, e.g. aliminium stearate, to delay absorption within the body. Such oily solutions have a very prolonged activity when injected intramuscularly, and satisfactory neuroleptic action has been produced by a single intramuscular injection of about 25–40 mg of a compound of Formula I dissolved in a light vegetable oil for as long as 2–6 weeks.

The preferred compound of Formula I for use in the pharmaceutical compositions according to the invention is the behenic acid ester of 2-trifluoromethyl-7-fluoro-10-(3'-(4-(2-hydroxyethyl)-1-piperidyl)propyl)-phenothiazine, in the following called Lu 12-112 for short.

The following examples illustrate the injectable oily solutions according to the present invention:

| | | | |
|---|---|---|---|
| 1. Lu 13-112 | | 16 | grams |
| Sterile, light vegetable oil | ad | 1000 | ml |
| 2. Lu 13-112 | | 32 | grams |
| Sterile sesame oil | ad | 1000 | ml |
| 3. Lu 13-112 | | 100 | grams |
| Aluminium mono stearate | | 20 | grams |
| Sterile, light vegetable oil | ad | 1000 | ml |
| 4. Lu 13-112 | | 16 | grams |
| Sterile olive oil | ad | 1000 | ml |

The solutions are filled in for example ampoules each containing 1 ml solution.

The active ingredient of Formula I may also be administered in the form of a suspension of micronized active ingredient or a salt thereof in sterile physiologically saline.

Any other pharmaceutical adjuvants may be used provided that they are compatible with the active ingredient, and additional compositions and dosage forms may be similar to those presently used for neuroleptics. Also combinations of a compound of Formula I as well as its pharmacologically acceptable non-toxic acid addition salts with other active ingredients especially other neuroleptics, thymoleptics or the like fall within the scope of the present invention.

When testing the behenic acid esters of Formula I it has been found advantageous to use the well recognized test which is based upon the fact that strong neuroleptics antagonize apomorphine induced vomiting in dogs. The test is described by P. A. J. Janssen, C. J. E. Niemegeers and K. H. L. Schellehaus: "Is it possible to predict the clinical effects of neuroleptic drugs (major tranquilisers) from animal data,"? Part II, Arzneimittel Forschung, 15, 1196-1206, 1965. In order to evaluate esters of the compounds of Formula I a modified method is described by M. Nymark et al. in Acta pharmacol. et toxicol. 1973, 33, 363–376. The test may be described shortly as follows:

Apomorphine antagonism in dogs

As animals were used adult purebred Beagle dogs of either sex. The threshold-dose of apomorphine hydrochloride for the induction of vomiting in the dogs has been determined to be 0.025 mg/kg intravenously. After this dose vomiting occurs within a few minutes of the injection. Four dogs were used for each dose level of the drug, which was injected subcutaneously at the back of the neck. At different times after the drug administration the dogs were then challenged with apomorphine according to an "up-and-down" schedule using the dose-range 0.025 - 0.400 mg/kg intravenously geometrically spaced. Thus, if for example a dog vomited after 0.1 mg/kg the next dog was given 0.05 mg/kg or 0.2 mg/kg if the first dog did not vomit, and so on. In this way it was possible to estimate at which level of apomorphine the dogs were protected at a given time. The dogs were fed half an hour before testing to ensure an easy vomiting.

Esters such as the enanthic and decanoic acid esters of strong neuroleptics have previously been suggested, and the enanthic acid ester of fluphenazin has, in fact, found use in recent years in the form of oily solutions for injection having sustained release effect. — It has now been found that Lu 13-112 seems to be more favourable than the corresponding palmitic ester (Lu 13-113) and considerably more favourable than the said enanthic acid ester of fluphenazin. Lu 13-112 (1.6 mg/kg s.c.) protected the dogs against vomiting up to 21 days when injected as a solution in light vegetable oil without disturbing sedation and gave a maximal protection (12 × threshold dose), whereas Lu 13-113 protected the dogs up to 16 days and caused considerable sedation in the first week. Fluphenazin enanthate protected the dogs up to 14 days and gave only a maximal protection of 3 × threshold dose with no appreciable sedation in the first week.

We claim:

1. A compound selected from the group consisting of 1) a behenic acid ester of the following formula:

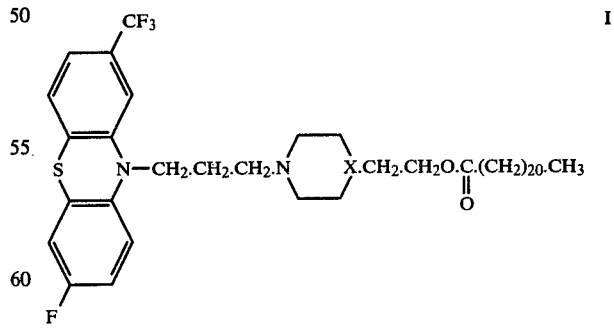

wherein X is selected from "N" and "CH," and 2) an acid addition salt thereof with a pharmaceutically acceptable acid.

2. A behenic acid ester according to claim 1 of the following formula:

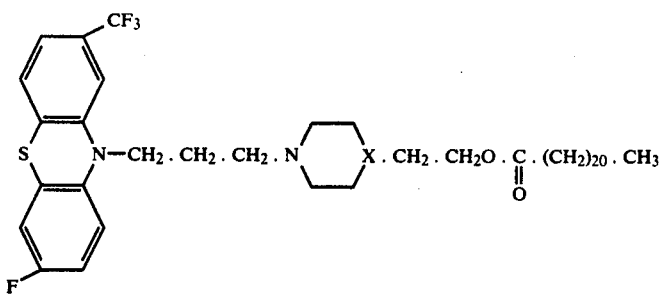

wherein X is selected from "N" and "CH".

3. A behenic acid ester according to claim 1 or 2 of the following formula

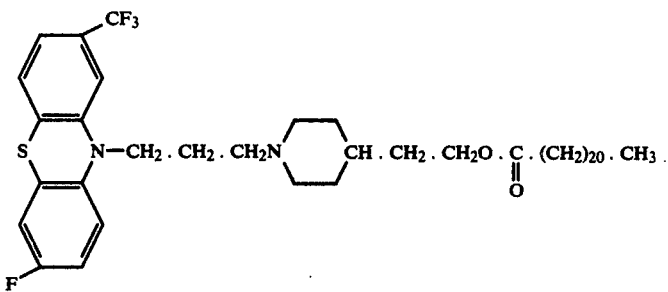

4. A behenic acid ester according to claim 1 or 2 of the following formula:

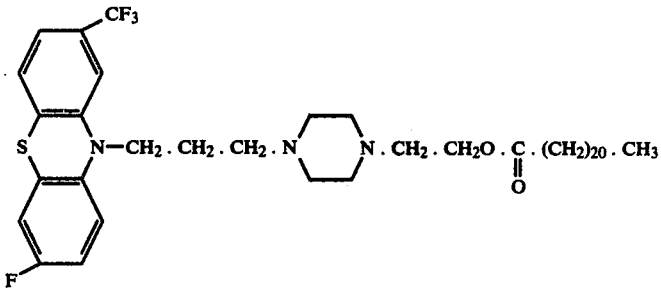

5. A pharmaceutical composition comprising a major quantity of a pharmaceutical carrier and a pharmaceutically effective dose of a compound as defined in claim 1.

6. A composition according to claim 5, wherein the active ingredient is the behenic acid ester of 2-trifluoromethyl-7-fluoro-10-(3'-(4-(2-hydroxyethyl)-1-piperidyl)propyl)phenothiazine.

7. A method for the treatment of psychotic disorders in a living animal subject in need of such treatment, comprising the steps of administering to the said subject in need of said treatment a neuroleptically-effective amount of a compound as defined in claim 1.

8. The method of claim 7, wherein the neuroleptically-active compound is administered in an amount of from 0.01 mg to 100 mg per unit dose, calculated as the free base.

9. The method of claim 7, wherein the neuroleptically-active compound is the behenic acid ester of 2-trifluoromethyl-7-fluoro-10-(3'(4-(2-hydroxyethyl)-1-piperidyl)propyl)phenothiazine, or a pharmaceutically-acceptable acid addition salt thereof.

10. The method of claim 7, wherein the neuroleptically-active compound is administered in an amount of about 0.01 mg to 10 mg per kg of body weight per unit dose.

* * * * *

UNITED STATES PATENT AND TRADEMARK OFFICE
CERTIFICATE OF CORRECTION

PATENT NO. : 4,153,694

DATED : May 8, 1979

INVENTOR(S) : Buus et al.

It is certified that error appears in the above–identified patent and that said Letters Patent are hereby corrected as shown below:

Col. 1, line 37; "(3'-(4-2-" should read -- (3'-(4-(2- --

Signed and Sealed this

Twenty-fourth Day of July 1979

[SEAL]

Attest:

LUTRELLE F. PARKER

Attesting Officer     Acting Commissioner of Patents and Trademarks